| United States Patent [19] | [11] Patent Number: 4,783,450 |
| Fawzi et al. | [45] Date of Patent: Nov. 8, 1988 |

[54] USE OF COMMERCIAL LECITHIN AS SKIN PENETRATION ENHANCER

[75] Inventors: Mahdi B. Fawzi, Flanders; Uma R. Iyer, Mendham; Majid Mahjour, Netcong, all of N.J.

[73] Assignee: Warner-Lambert Company, Morris Plains, N.J.

[21] Appl. No.: 37,671

[22] Filed: Apr. 13, 1987

[51] Int. Cl.$^4$ .......................................... A61V 31/685
[52] U.S. Cl. ..................................... 514/78; 514/946; 514/969
[58] Field of Search ................. 514/940, 947, 969, 78

[56] References Cited

U.S. PATENT DOCUMENTS 4,364,930 12/1982 Griat et al. ........................... 424/81

FOREIGN PATENT DOCUMENTS 2001334 3/1982 United Kingdom .

OTHER PUBLICATIONS

J. Pharm. Pharmacology, 1987; 39:399–400, Kato et al.
Chem. Abst. (1976)–84–79639f.
Chem. Abst. (1984)–101–43606y.

*Primary Examiner*—Stanley J. Friedman
*Attorney, Agent, or Firm*—Ronald A. Daignault

[57] ABSTRACT

A method of enhancing penetration of a drug through the skin or other biological membranes using lecithin is herein described along with pharmaceutical compositions containing effective amounts of lecithin as a penetration enhancer.

6 Claims, No Drawings

USE OF COMMERCIAL LECITHIN AS SKIN PENETRATION ENHANCER

BACKGROUND OF THE INVENTION

Lecithin, as used in commerce, is the name given to a group of substances present in fats which are obtained mainly from oil seeds, for example, soybeans and rape seeds) and from egg yolks. Commercial lecithin is a natural emulsifying agent used in foodstuffs and pharmaceutical products, for example, in creams, balms, or ointments.

Lecithin has also been described in dispersions or suspensions in propellants. For example, broncho-dilators can be administered by inhalation means in a propellant containing lecithin.

It has now been found that lecithin enhances the penetration of a drug through the skin and across other biological membranes, such as intestinal, buccal, rectal, and nasal. Thus an object of the present invention is a method of administering a drug transdermally or transmucosally by using lecithin in the pharmaceutical composition.

SUMMARY OF THE INVENTION

Accordingly, the present invention relates to a process for enhancing penetration of a drug through the skin and other biological membranes which comprises applying to the skin or membrane of a host in need thereof a pharmaceutical composition containing an active ingredient and an effective amount of lecithin.

Another aspect of the present invention is a pharmaceutical composition adapted for transdermal or transmucosal administration comprising an active ingredient and an effective amount of lecithin.

DESCRIPTION OF PREFERRED EMBODIMENTS

Transdermal pharmaceutical compositions are used as a means for avoiding the uncertainties of oral administration and the inconvenience of administration by rejection.

An active ingredient for purposes of the present invention is an effective amount of any therapeutically active drug.

Preferred drugs are those which find application in various therapeutic uses such as antihypertensives, analgesics, antitussives, antihistamines, bronchodilators, cognition activators, and others. Therefore, the lecithin compositions are expected to be useful in drugs such as procaterol, dextromethorphan, oxymorphone, diphenhydramine, and others.

The lecithin employed in the present invention is commercial lecithin or soy lecithin, for example, Lucas Meyer, Inc. commercial soy lecithins such as Epikuron ™ 135F and Capcithin ™ 50-R. The amount of lecithin used in the transdermal formulations may vary depending on the amount of active ingredient needed and the use of other excipients. A useful range of lecithin found to be effective for penetration enhancement is about 2 to about 40% by weight of the composition. Preferred is from about 5 to about 10%.

The present composition also may contain pharmaceutically acceptable excipients. These are, for example, tetraglycol (TG), alcohols, glycols, fatty acids, triacetin, silicon fluids, and the like.

The following examples in table form are illustrative of the present invention where the use of commercial soy lecithin was found to enhance penetration of various drugs through mouse skin.

TABLE

| Formulation Number | Composition | Percent w/w | Drug Category | Flux ($\mu g/cm^2/h$) | Flux Value in Absence of Lecithin ($\mu g/cm^2/h$) |
| --- | --- | --- | --- | --- | --- |
| 1. | Procaterol<br>EP 135 F<br>TG | 2<br>10<br>88 | Bronchodilator | 93 | Negligible |
| 2. | CI-969*<br>EP 135 F<br>TG | 2<br>10<br>88 | Cognition Activator | 110 | 5 |
| 3. | Dextromethorphan<br>EP 135 F<br>TG | 2<br>10<br>88 | Antitussive | 214 | 10 |
| 4. | Dextromethorphan<br>Cap 50-R<br>TG | 2<br>10<br>88 | Antitussive | 119 | 10 |
| 5. | Oxymorphone<br>EP 135 F<br>TG | 4<br>10<br>86 | Analgesic | 25 | Negligible |
| 6. | Diphenhydramine<br>EP 135 F<br>TG | 10<br>20<br>70 | Antihistamine | 570 | ~100 |
| 7. | Diphenhydramine<br>EP 135 F<br>TG | 10<br>10<br>80 | Antihistamine | 1100 | ~100 |
| 8. | Diphenhydramine<br>Cap 50-R<br>TG | 10<br>10<br>80 | Antihistamine | 490 | ~100 |

Code:
EP 135 F = Epikuron ™ 135F (Lucas Meyer, Inc.)
TG = Tetraglycol
Cap 50-R = Capcithin ™ 50R (Lucas Meyer, Inc.)
*CI-969 = Ethanone,1-(1,2,5,6-tetrahydro-1-methyl-3-pyridinyl)-,O—acetyloxime.

We claim:

1. A process for enhancing penetration of a drug through the skin or other biological membranes which comprises administering to the skin or other biological membrane of a host in need thereof a pharmaceutical composition containing an effective amount of procaterol and an effective amount of commercial lecithin.

2. A process according to claim 1, wherein the effective amount of lecithin is 2 to 40%.

3. A process according to claim 1, wherein the effective amount of lecithin is 5 to 10%.

4. A pharmaceutical composition adapted for transdermal or transmucosal administration comprising an effective amount of procaterol, an effective amount of commercial lecithin, and one or more pharmaceutically acceptable excipients.

5. A composition according to claim 4, wherein the amount of lecithin is 2 to 40%.

6. A composition according to claim 4, wherein the amount of lecithin is 5 to 10%.

* * * * *